(12) United States Patent
Takeshima

(10) Patent No.: US 12,711,374 B2
(45) Date of Patent: Aug. 18, 2026

(54) DATA PROCESSING DEVICE, MAGNETIC RESONANCE IMAGING DEVICE, AND DATA PROCESSING METHOD

(71) Applicant: Canon Kabushiki Kaisha, Tokyo (JP)

(72) Inventor: Hidenori Takeshima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 848 days.

(21) Appl. No.: 17/930,190

(22) Filed: Sep. 7, 2022

(65) Prior Publication Data

US 2023/0070342 A1 Mar. 9, 2023

(30) Foreign Application Priority Data

Sep. 7, 2021 (JP) ................................ 2021-145703

(51) Int. Cl.
*G06N 3/08* (2023.01)
*G16H 30/20* (2018.01)

(52) U.S. Cl.
CPC ............... *G06N 3/08* (2013.01); *G16H 30/20* (2018.01)

(58) Field of Classification Search
CPC ........................................................ G06N 3/08
USPC ............................................................ 706/23
See application file for complete search history.

(56) References Cited

U.S. PATENT DOCUMENTS 10,393,834 B2 * 8/2019 Kuratani .............. G01R 33/546
11,540,798 B2 * 1/2023 Huang .................. A61B 6/037
11,589,888 B2 * 2/2023 Shelton, IV ........... G16H 70/20
2019/0213761 A1 * 7/2019 Rosen .................... G06V 10/82
2019/0333227 A1 * 10/2019 Zhang .................. G06F 18/217
2019/0369191 A1 * 12/2019 Gong ................ G01R 33/5608
2020/0042873 A1 * 2/2020 Daval Frerot ........... G06N 3/08
2020/0126190 A1 * 4/2020 Lebel ........................ G06T 5/60
2020/0249306 A1 * 8/2020 Abdishektaei ....... G06N 3/0464
2021/0290191 A1 * 9/2021 Qi ......................... A61B 6/5258
2022/0375209 A1 * 11/2022 Kutsuna ................... G06N 3/09
2023/0070342 A1 * 3/2023 Takeshima ............. G16H 30/40
2023/0130481 A1 * 4/2023 Kutsuna ................. G06N 3/084 324/307
2023/0342886 A1 * 10/2023 Meyer ...................... G06T 5/70

(Continued)

FOREIGN PATENT DOCUMENTS

JP 2000-166892 A 6/2000
JP 2015-188635 A 11/2015
JP 2018-136419 A 8/2018

OTHER PUBLICATIONS

Koonjoo et al., "Boosting the signal-to-noise of low-field MRI with deep learning image reconstruction," Scientific Reports, vol. 11, No. 8248, 2021, 16 pages.

(Continued)

*Primary Examiner* — Reza Nabi
(74) *Attorney, Agent, or Firm* — Oblon, McClelland, Maier & Neustadt, L.L.P.

(57) ABSTRACT

A data processing device according to an embodiment generates output data by inputting, to a learned model, as input data, first input data of a complex value and second input data that is data related to a complex phase, the learned model having been trained using, as input data, first input data for learning of a complex value obtained based on collected data collected by a medical image diagnostic device and second input data for learning that is data related to a complex phase of the collected data, and using, as output data, output data for learning.

11 Claims, 6 Drawing Sheets

(56) References Cited

U.S. PATENT DOCUMENTS

| | | | | |
|---|---|---|---|---|
| 2024/0005481 | A1* | 1/2024 | Haji-Valizadeh | G06N 3/045 |
| 2024/0104798 | A1* | 3/2024 | Gubbi Lakshminarasimha | G06T 12/10 |
| 2024/0296524 | A1* | 9/2024 | Pfaff | G06T 5/70 |
| 2025/0191139 | A1* | 6/2025 | Tamir | G06T 5/60 |
| 2025/0194946 | A1* | 6/2025 | Shepherd | G01R 33/5608 |

OTHER PUBLICATIONS

Japanese Office Action issued Mar. 12, 2025 in Japanese Patent Application No. 2021-145703, 5 pages.
Trabelsi, C. et al. "Deep Complex Networks" arXiv:1705.09792v4 [cs.NE] published as a conference paper at ICLR 2018. (19 pages).

* cited by examiner

100
DATA PROCESSING DEVICE
134
INPUT DEVICE
132
MEMORY
135
DISPLAY
110
PROCESSING CIRCUIT
110a
TRAINING DATA CREATION FUNCTION
110b
LEARNING FUNCTION
110c
INTERFACE FUNCTION
110d
CONTROL FUNCTION
110e
APPLICATION FUNCTION
110f
ACQUISITION FUNCTION
110g
FIRST DATA GENERATION FUNCTION
110h
SECOND DATA GENERATION FUNCTION

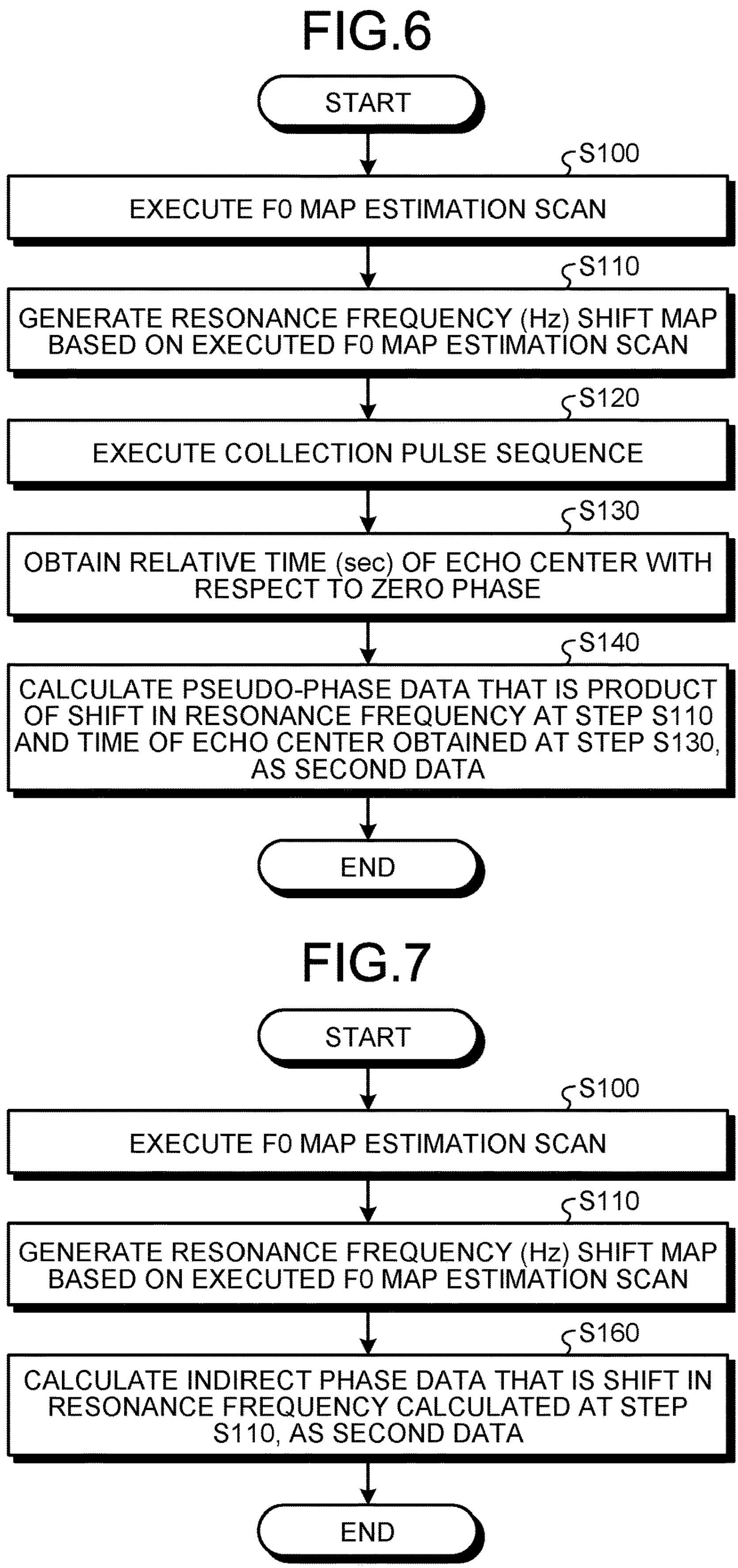
FIG.6
START
S100
EXECUTE F0 MAP ESTIMATION SCAN
S110
GENERATE RESONANCE FREQUENCY (Hz) SHIFT MAP BASED ON EXECUTED F0 MAP ESTIMATION SCAN
S120
EXECUTE COLLECTION PULSE SEQUENCE
S130
OBTAIN RELATIVE TIME (sec) OF ECHO CENTER WITH RESPECT TO ZERO PHASE
S140
CALCULATE PSEUDO-PHASE DATA THAT IS PRODUCT OF SHIFT IN RESONANCE FREQUENCY AT STEP S110 AND TIME OF ECHO CENTER OBTAINED AT STEP S130, AS SECOND DATA
END
FIG.7
START
S100
EXECUTE F0 MAP ESTIMATION SCAN
S110
GENERATE RESONANCE FREQUENCY (Hz) SHIFT MAP BASED ON EXECUTED F0 MAP ESTIMATION SCAN
S160
CALCULATE INDIRECT PHASE DATA THAT IS SHIFT IN RESONANCE FREQUENCY CALCULATED AT STEP S110, AS SECOND DATA
END 200
MAGNETIC RESONANCE IMAGING DEVICE
Y
Z
X
100
DATA PROCESSING DEVICE
220
SEQUENCE CONTROL CIRCUIT
204
GRADIENT MAGNETIC FIELD POWER SUPPLY
210
RECEIVER CIRCUIT
208
TRANSMITTER CIRCUIT
206
COUCH CONTROL CIRCUIT
201
203
207
209
P
205a
205
207
203
201

DATA PROCESSING DEVICE, MAGNETIC RESONANCE IMAGING DEVICE, AND DATA PROCESSING METHOD

CROSS-REFERENCE TO RELATED APPLICATIONS

This application is based upon and claims the benefit of priority from Japanese Patent Application No. 2021-145703, filed on Sep. 7, 2021; the entire contents of which are incorporated herein by reference.

FIELD

Embodiments described herein relate generally to a data processing device, a magnetic resonance imaging device, and a data processing method.

BACKGROUND

In machine learning using a neural network, a real-valued neural network is used as a standard.

However, in the medical data processing device such as a magnetic resonance imaging device and an ultrasonic diagnostic device, signal processing using complex numbers is often used. Hence, various applications are possible by using a complex-valued neural network.

However, in neural networks using complex numbers, phase components may cause image quality degradation.

BRIEF DESCRIPTION OF THE DRAWINGS

FIG. 6 is a diagram for explaining the procedure of obtaining second data in the neural network according to the embodiment;

FIG. 7 is a diagram for explaining the procedure of obtaining second data in the neural network according to the embodiment;

DETAILED DESCRIPTION

Embodiment

Figure 1:
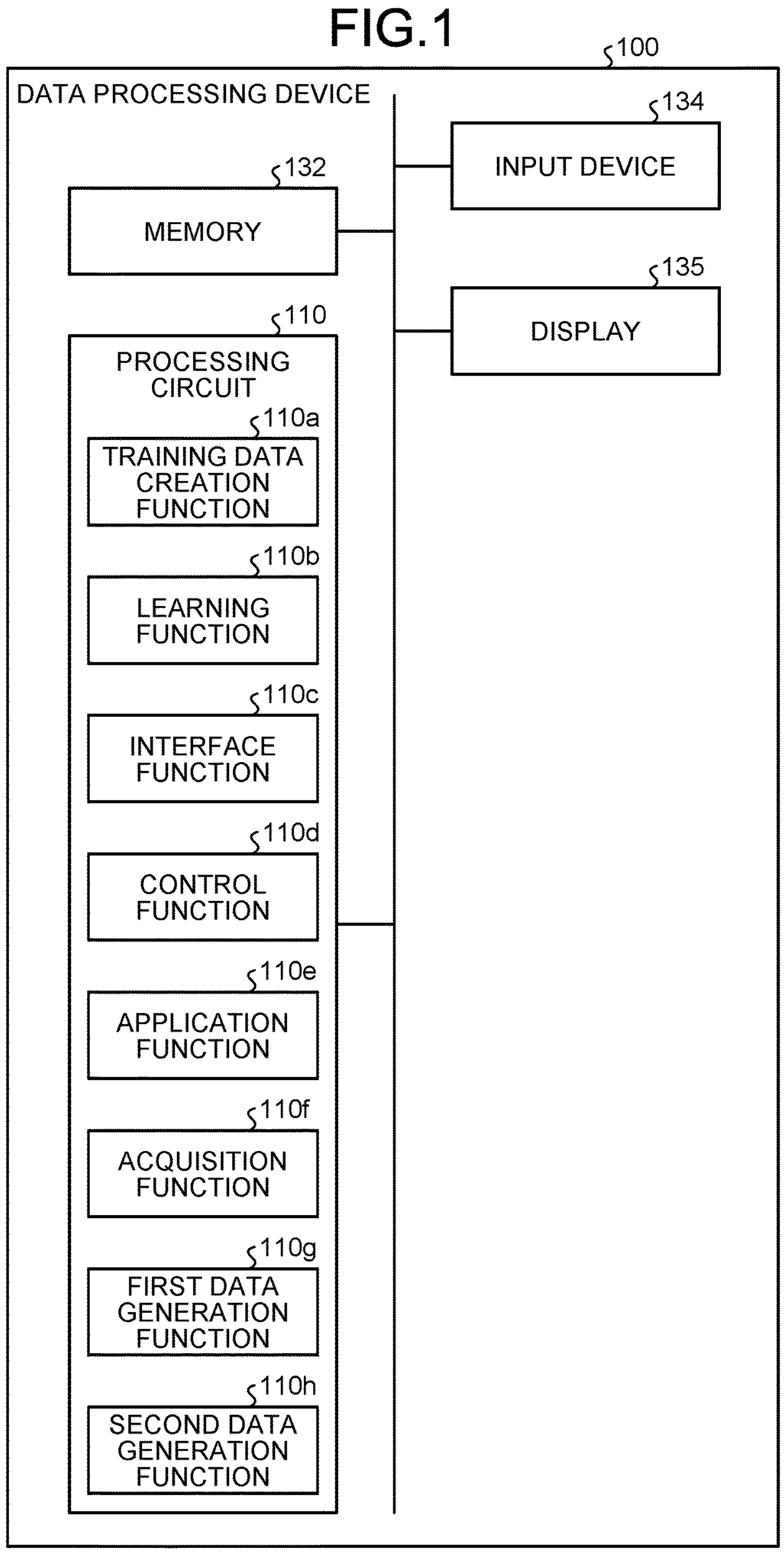
FIG. 1 is a diagram illustrating an example of a data processing device according to an embodiment.

A data processing device provided in one aspect of the present invention generates output data by inputting, to a learned model, as input data, first input data of a complex value and second input data that is data related to a complex phase, the learned model having been trained using, as input data, first input data for learning of a complex value obtained based on collected data collected by a medical image diagnostic device and second input data for learning that is data related to a complex phase of the collected data, and using, as output data, output data for learning.

Hereinafter, an embodiment of a data processing device, a magnetic resonance imaging device, and a data processing method will be described in detail with reference to the accompanying drawings.

First, with reference to FIG. 1, a configuration of a data processing device 100 according to the embodiment will be described.

The data processing device 100 includes a processing circuit 110, a memory 132, an input device 134, and a display 135. The processing circuit 110 includes a training data creation function 110*a*, a learning function 110*b*, an interface function 110*c*, a control function 110*d*, an application function 110*e*, an acquisition function 110*f*, a first data generation function 110*g*, and a second data generation function 110*h*.

In the embodiment, each processing function performed by the training data creation function 110*a*, the learning function 110*b*, the interface function 110*c*, the control function 110*d*, the application function 110*e*, the acquisition function 110*f*, the first data generation function 110*g*, and the second data generation function 110*h*, and a learned model (for example, a neural network) are stored in the memory 132 in the form of computer executable programs. The processing circuit 110 is a processor that implements a function corresponding to each computer program, by reading a computer program from the memory 132 and executing the computer program. In other words, the processing circuit 110 in a state in which each computer program is read has each function illustrated in the processing circuit 110 in FIG. 1. Moreover, the processing circuit 110 in a state in which a computer program corresponding to a learned model (neural network) is read can perform the processing according to the learned model. In FIG. 1, the functions of the processing circuit 110 are implemented by a single processing circuit. However, the functions of the processing circuit 110 may also be implemented by configuring the processing circuit 110 by combining a plurality of independent processors, and causing each of the processors to execute a computer program. In other words, each of the functions described above may be configured as a computer program, and a single processing circuit may execute each computer program. Moreover, a single processing circuit may implement two or more functions of the processing circuit 110. As another example, a specific function may be implemented in a dedicated independent program execution circuit.

In FIG. 1, the processing circuit 110, the training data creation function 110*a*, the learning function 110*b*, the interface function 110*c*, the control function 110*d*, the application function 110*e*, the acquisition function 110*f*, the first data generation function 110*g*, and the second data generation function 110*h* are examples of a processing unit, a creation unit, an input unit (learning unit), a receiver unit, a control unit, an application unit, an acquisition unit, a first generation unit, and a second generation unit, respectively.

For example, the term "processor" used in the above description refers to a central processing unit (CPU), a graphical processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements the function by reading and executing a computer program stored in the memory 132.

Moreover, instead of storing a computer program in the memory 132, the computer program may also be directly incorporated in a circuit of the processor. In this case, the processor implements the function by reading and executing a computer program incorporated in the circuit. Thus, for example, instead of storing a learned model in the memory 132, a computer program according to the learned model may be directly incorporated in the circuit of the processor.

With the training data creation function 110*a*, the processing circuit 110 generates training data for learning, on the basis of the data, signals, and images acquired by the interface function 110*c*.

With the learning function 110*b*, the processing circuit 110 generates a learned model, by performing learning using the training data generated by the training data creation function 110*a*.

With the interface function 110*c*, the processing circuit 110 acquires the data, signals, images, and the like for signal generation of the application function 110*e*, from the memory 132.

With the control function 110*d*, the processing circuit 110 controls the overall processing of the data processing device 100. More specifically, with the control function 110*d*, the processing circuit 110 controls the processing of the processing circuit 110, on the basis of various setting requests input from an operator via the input device 134, and various control programs and various types of data read from the memory 132.

Moreover, with the application function 110*e*, the processing circuit 110 generates a signal on the basis of the results of processing performed using the training data creation function 110*a* and the learning function 110*b*. Furthermore, with the application function 110*e*, the processing circuit 110 applies the learned model generated by the learning function 110*b* to an input signal, and generates a signal on the basis of the application results of the learned model.

The memory 132 includes a semiconductor memory element such as a random access memory (RAM) and a flash memory, a hard disk, an optical disc, and the like. The memory 132 is a memory that stores data such as signal data for display and signal data for training generated by the processing circuit 110.

The memory 132 stores various types of data such as a control program for signal processing and display processing, as necessary.

The input device 134 receives various instructions and information input by the operator. For example, the input device 134 is a pointing device such as a mouse or a trackball, a selection device such as a mode change-over switch, or an input device such as a keyboard.

Under the control of the control function 110*d* and the like, the display 135 displays a graphical user interface (GUI) for receiving an input of imaging conditions, a signal generated by the control function 110*d*, and the like. For example, the display 135 is a display device such as a liquid crystal display. The display 135 is an example of a display unit. The display 135 includes a mouse, a keyboard, a button, a panel switch, a touch command screen, a foot switch, a trackball, a joystick, and the like.

Subsequently, with reference to FIGS. 2 to 4, a configuration of the neural network according to the embodiment will be described.

Figure 2:
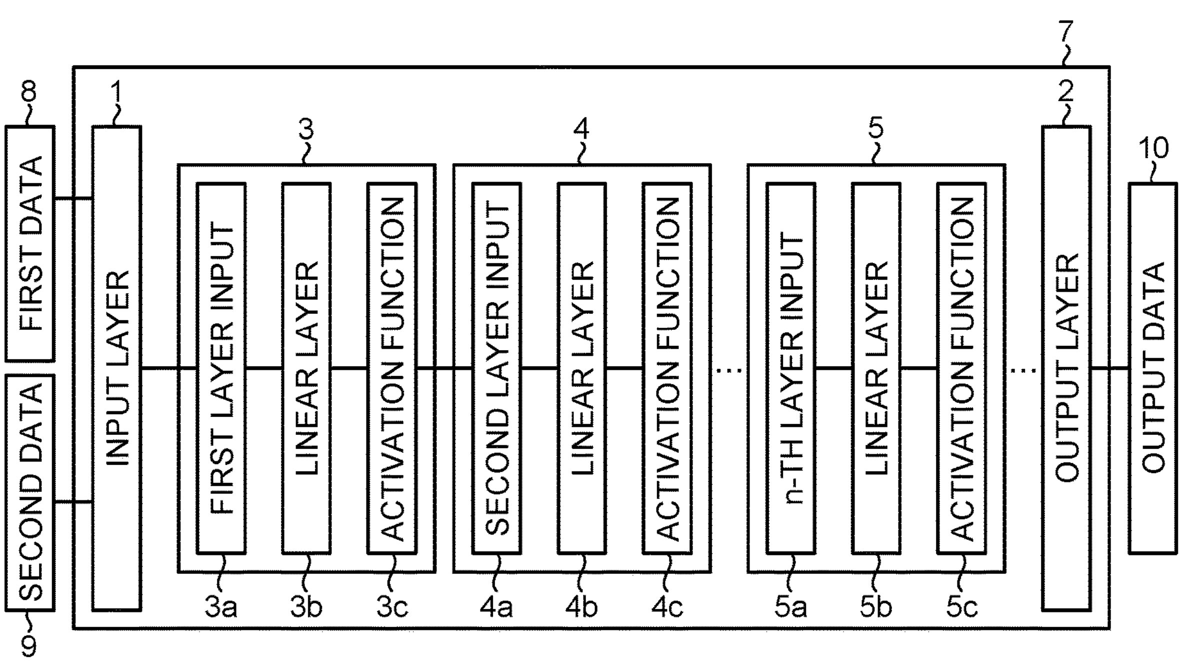
FIG. 2 is a diagram illustrating an example of a neural network according to the embodiment.
Figure 3:
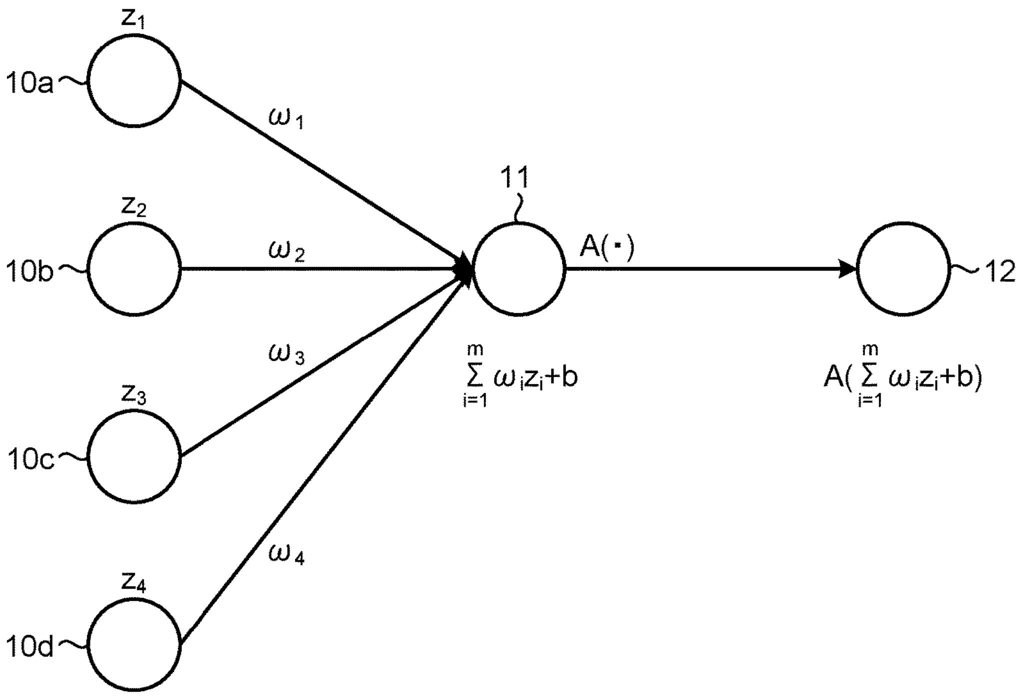
FIG. 3 is a diagram for explaining a neural network according to the embodiment.

FIG. 2 illustrates an example of the interconnections between layers in a neural network 7 used for machine learning by the processing circuit 110 with the learning function 110*b*. The neural network 7 includes an input layer 1, an output layer 2, and intermediate layers 3, 4, 5, and the like between the input layer 1 and the output layer 2. Each of the intermediate layers includes a layer related to each input (hereinafter, referred to as an input layer in each layer), a linear layer, and a layer according to the process using an activation function (hereinafter, referred to as an activation layer). For example, the intermediate layer 3 includes an input layer 3*a*, a linear layer 3*b*, and an activation layer 3*c*. The intermediate layer 4 includes an input layer 4*a*, a linear layer 4*b*, and an activation layer 4*c*. The intermediate layer 5 includes an input layer 5*a*, a linear layer 5*b*, and an activation layer 5*c*. Moreover, each layer includes multiple nodes (neurons).

In this example, to the complex-valued medical data, the data processing device 100 according to the embodiment applies a linear layer with a complex number coefficient and nonlinear activation (activation function). That is, to the complex-valued medical data, with the learning function 110*b*, the processing circuit 110 generates a learned model by training the neural network 7 to which a linear layer with a complex number coefficient and nonlinear activation (activation function) are applied. For example, the processing circuit 110 stores the generated learned model in the memory 132 as necessary.

Moreover, first data 8 that is input data of a complex value obtained on the basis of the data collected by a medical image diagnostic device, and second data 9 that is data related to a complex phase of the collected data, are input to the input layer 1. The first data 8 and the second data 9 will be described below.

Furthermore, for example, the data output from the output layer 2 is complex number data from which noise is removed.

If the neural network 7 according to the embodiment is a convolutional neural network (CNN), for example, the data input to the input layer 1 is data represented by a two-dimensional array of size 32×32 or the like, and for example, the data output from the output layer 2 is data represented by a two-dimensional array of size 32×32 or the like. The size of the data input to the input layer 1 and the size of the data output from the output layer 2 may be the same or different. Similarly, the number of nodes in the intermediate layer may be the same or different from the number of nodes in the layers before and after the intermediate layer.

Subsequently, generation of the learned model according to the embodiment, that is, a learning step will be described. For example, with the learning function 110*b*, the processing circuit 110 generates a learned model by carrying out machine learning on the neural network 7. In this example, to carry out machine learning means to determine the weights in the neural network 7 including the input layer 1, the intermediate layers 3, 4, and 5, and the output layer 2, for example. More specifically, to carry out machine learning means to determine a set of coefficients that characterizes the connection between the input layer 1 and the intermediate layer 3, a set of coefficients that characterizes the connection between the intermediate layer 3 and the intermediate layer 4, . . . , and a set of coefficients that characterizes the connection between the intermediate layer 5 and the output layer 2. For example, with the learning function 110*b*, the processing circuit 110 determines these sets of coefficients, using a back propagation method.

With the learning function 110*b*, the processing circuit 110 carries out machine learning on the basis of training data that is supervised data including data input to the input layer 1 and data output to the output layer 2, determines the weights between the layers, and generates a learned model in which the weights are determined.

In deep learning, self-encoding (autoencoder) can be used. In this case, the data required for machine learning need not be supervised data.

Subsequently, a process of applying the learned model according to the embodiment will be described. First, for example, with the application function 110*e*, the processing circuit 110 inputs an input signal to the learned model. For example, with the application function 110*e*, the processing circuit 110 inputs an input signal to the input layer 1 of the neural network 7, that is, the learned model. Subsequently, with the application function 110*e*, the processing circuit 110 obtains the data output from the output layer 2 of the neural network 7, that is, the learned model, as an output signal. For example, the output signal is a signal on which a predetermined process such as noise removal is performed. In this manner, for example, with the application function 110*e*, the processing circuit 110 generates the output signal on which a predetermined process such as noise removal is performed. As necessary, with the control function 110*d*, the processing circuit 110 may also display the acquired output signal on the display 135.

Returning to the description of the activation function and the activation layer, an activation function in the neural network 7 will be described with reference to FIG. 3. In FIG. 3, nodes 10*a*, 10*b*, 10*c*, and 10*d* are some nodes in the input layer of a certain layer cut out and displayed. On the other hand, a node 11 is one of the nodes in the linear layer, and a node 12 is one of the nodes in the activation layer that is a layer according to the process (activation) using an activation function.

In this example, in a case when the output values of the nodes 10*a*, 10*b*, 10*c*, and 10*d* are complex numbers $z_1$, $z_2$, $z_3$, and $z_4$, the output result to the node 11 in the linear layer is given by $\Sigma_{i=1}^{m}(\omega_i z_i+b)$. In this example, $\omega_i$ is a weighting coefficient between the i-th input layer and the node 11, m is the number of nodes to which the node 11 is connected, and b is a predetermined constant. Subsequently, if y be the output result output to the node 12 that is an activation layer, y is expressed by the following formula (1) using an activation function A.

$$y = A\left(\sum_{i=1}^{m}\omega_i x_i + b\right) \tag{1}$$

In this example, the activation function A is usually a nonlinear function. For example, a sigmoid function, a tanh function, a rectified linear unit (ReLU), or the like is selected as the activation function A.

Figure 4:
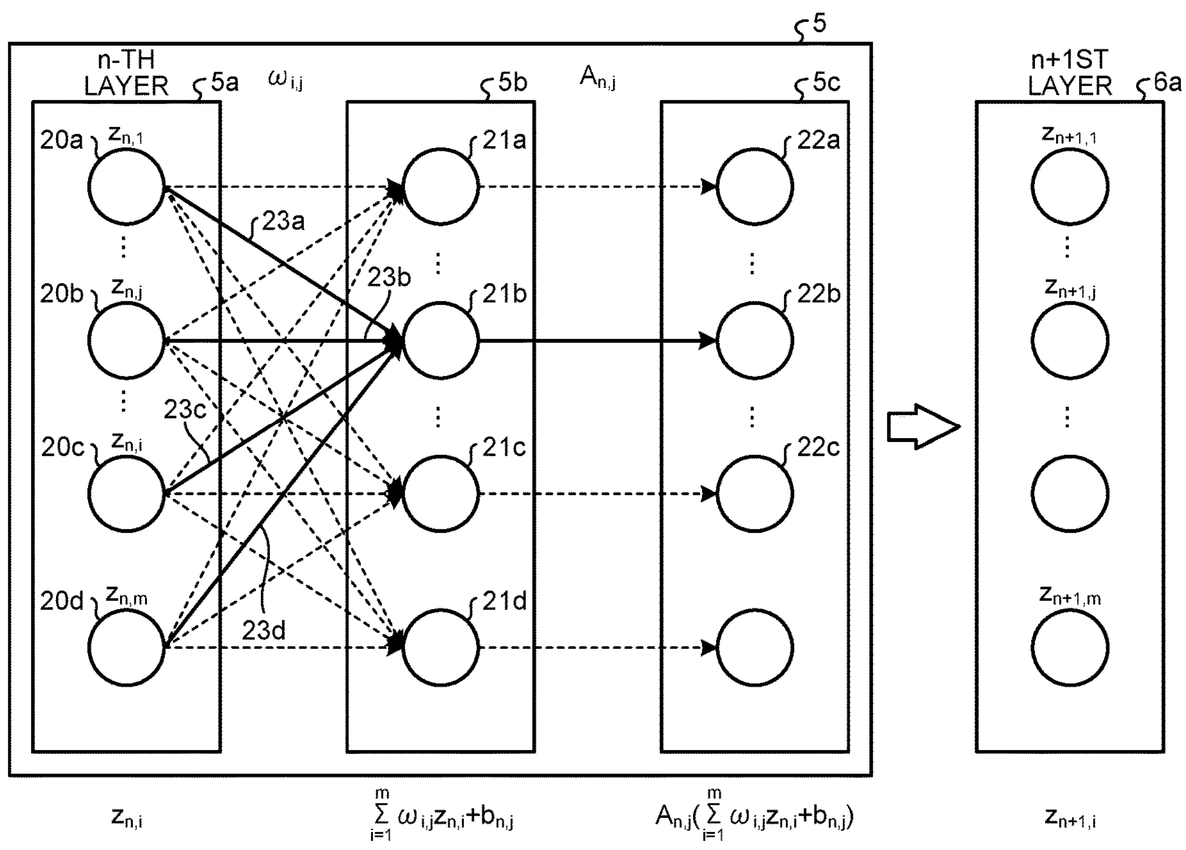
FIG. 4 is a diagram for explaining a neural network according to the embodiment.

FIG. 4 illustrates the process using such an activation function. In FIG. 4, the intermediate layer 5 is the n-th layer in the neural network 7, and includes the input layer 5*a*, the linear layer 5*b*, and the activation layer 5*c*. An input layer 6*a* is the n+1st layer in the neural network. Moreover, the input layer 5*a* includes nodes 20*a*, 20*b*, 20*c*, 20*d*, and the like, the linear layer 5*b* includes nodes 21*a*, 21*b*, 21*c*, 21*d*, and the like, and the activation layer 5*c* includes nodes 22*a*, 22*b*, 22*c*, and the like. Furthermore, FIG. 4 illustrates a real-valued neural network in which each node has a real value, and the input result $z_{n,i}$ to the input layer 5*a*, and the output result $z_{n+1,i}$ of the input layer 6*a* are complex numbers.

In this example, the output result to the linear layer 5*b* is calculated by performing a predetermined weighted addition to each node in the input layer 5*a*. For example, the output result to the j-th node 21*b* in the linear layer 5*b* is given by $\Sigma_{i=1}^{m}\omega_{i,j}z_{n,i}+b_{n,j}$. In this example, $\omega_{i,j}$ is a weighting coefficient between the i-th input layer and the j-th linear layer, and $b_{n,j}$ is a predetermined constant known as a bias term. Subsequently, the output result to the activation layer 5*c* is calculated by applying the activation function A to each node in the linear layer 5*b*. For example, as expressed by the following formula (2), the output to the j-th node 22*b* in the activation layer 5*c* is given by $A_{n,j}(\Sigma_{i=1}^{m}\omega_{i,j}z_{n,i}+b_{n,j})$ using an activation function $A_{n,j}$.

$$z_{n+1,j} = A_{n,j}\left(\sum_{i=1}^{m}\omega_{i,j}z_{n,i} + b_{n,j}\right) \tag{2}$$

Subsequently, on the basis of the value output from the node in the activation layer 5*c*, the value of each node in the input layer 6*a* of the n-th layer is determined. As an example, the value of each node in the activation layer 5*c* is input directly to each node in the input layer 6*a*. Moreover, as another example, each node in the input layer 6*a* may be determined by further applying a nonlinear function to the activation layer 5*c*.

Subsequently, the background according to the embodiment will be described.

In machine learning using a neural network, a real-valued neural network is often used. However, in the signal processing field, for example, complex-valued representation is sometimes used to deal with two components of alternating current signal intensity and time in a unified manner. In such a case, various applications are possible by using a complex-valued neural network instead of a real-valued neural network.

However, in the neural networks using complex numbers, phase components may cause image quality degradation.

For example, the absolute value of the phase component is often not important, and for example, in the phase rotation operation, an important portion of an output image often remains unchanged. However, it is sometimes difficult to express the phase rotation operation by the neural network framework. For example, nonlinear transformations such as ReLU and ComplexReLU are used in the neural networks. However, since these nonlinear transformations are not symmetric with respect to the phase rotation, the output result of the phase rotation operation may not be stabilized. As described above, if a complex-valued neural network is simply used without taking into consideration physical factors of the complex phase in the image, the quality of the output image may be degraded.

Figure 5:
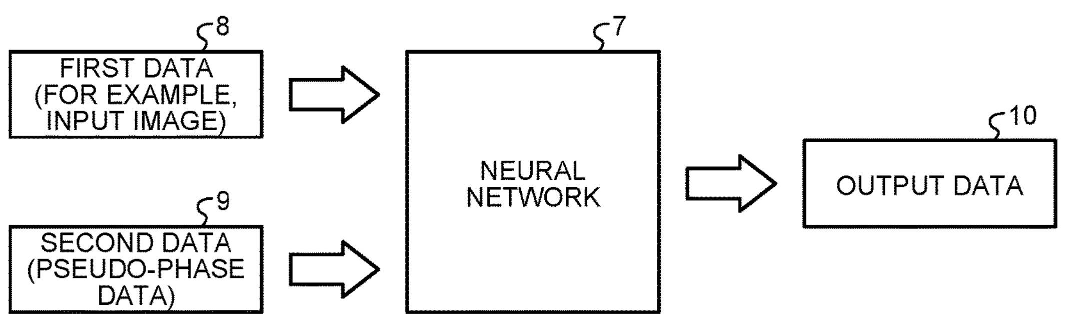
FIG. 5 is a diagram for explaining an example of a configuration of a neural network according to the embodiment.

Therefore, in the data processing device 100 according to the embodiment, as illustrated in FIG. 5, the quality of the output image of the neural network is improved, by inputting the second data 9 that is phase estimation information obtained by estimating in advance the complex phase of the collected data in the neural network 7, with the first data 8 that is the collected data.

In other words, in the data processing device 100 according to the embodiment, learning is performed by using, as input data input to the neural network 7, the second data 9 that is the second input data for learning and that is data related to a complex phase of data collected by the medical image diagnostic device, in addition to the first data 8 that is first input data for learning of a complex value obtained on the basis of the collected data, and using, as output data, output data 10 that is output data for learning.

The data processing device 100 outputs the output data 10, by inputting the first input data 8 of a complex value and the second input data 9 related to a complex phase to the learned model that has been trained, as input data. As a result, it is possible to improve the quality of the output image.

The neural network 7 according to the embodiment can be applied to solve various problems such as denoising and segmentation.

For example, the neural network 7 can be used for denoising. In this case, the output data for learning that is the output data 10, is data from which noise is reduced compared to the input data for learning that is the first data 8.

Moreover, for example, the neural network 7 may also be used for segmentation. In this case, the output data for learning that is the output data 10, is data representing the segment information at each location in the input data for learning that is the first data.

Furthermore, the learned model according to the embodiment can execute various types of image reconstruction methods using the neural network 7. For example, the embodiment can be applied to denoising image reconstruction, alternating direction method of multipliers (ADMM) image reconstruction, and automated transform by manifold approximation (AUTOMAP) image reconstruction.

In this example, the ADMM image reconstruction is one of iterative reconstruction methods that takes data consistency into consideration. The AUTOMAP image reconstruction is one of methods that links sensor data with an output image using appropriate training data through a supervised image task, by using manifold approximation. That is, the learned model according to the embodiment may be a learned model that generates output data by taking data consistency into consideration. Alternatively, the learned model according to the embodiment may also be a learned model to which an automated transform by manifold approximation (AUTOMAP) method is applied.

A process of applying the learned model according to the embodiment will now be described. First, with the application function 110*e*, the processing circuit 110 inputs an input image such as a medical image and medical image data to the learned model as the first data 8. In addition to the above, the processing circuit 110 also inputs pseudo-phase data obtained by a method, which will be described below, in FIG. 6, FIG. 7, and the like, to the learned model as the second data 9.

FIG. 6 and FIG. 7 describe the second data 9 serving as input data for learning during training. The second data 9 serving as input data applied to the learned model can also be obtained by performing the same process as that of the second data 9 serving as input data for learning during training.

In this manner, for example, when the first data 8 and the second data 9 are input to the neural network 7, with the application function 110*e*, the processing circuit 110 inputs the input data to the input layer 1 of the neural network 7, that is, the learned model. Subsequently, with the application function 110*e*, the processing circuit 110 obtains the data output from the output layer 2 of the neural network 7, that is, a learned model, as an output signal. For example, the output signal is a signal on which a predetermined process such as noise removal is performed. In this manner, for example, with the application function 110*e*, the processing circuit 110 generates the output signal on which a predetermined process such as noise removal is performed. As necessary, with the control function 110*d*, the processing circuit 110 may also display the acquired output signal on the display 135.

Returning to the learned model during training, the second data 9 (second input data for learning) input to the neural network 7 will now be described. The second data 9 input to the neural network 7 is estimated phase information that is input to the neural network as additional information. Typically, the second data 9 is defined for each pixel, and is an estimated value $\theta$ of a phase with a value ranging from $-\pi$ to $-\pi$. However, for example, the second data 9 may also take a value from $-1$ to 1. Moreover, the second data 9 need not necessarily be the estimated value of the phase, and may also be a scaling coefficient related to the phase, for example, a coefficient obtained by taking sin or cos of a phase $\theta$. Furthermore, the second data 9 need not necessarily be an accurate estimated value of the phase $\theta$, and input data useful for the training of the neural network 7 may also be sufficiently used. For example, the second data 9 may be information such as a roughly estimated value of the size of the phase $\theta$ or an indirect value indicating the size of the phase $\theta$.

Hereinafter, with reference to FIG. 6 and FIG. 7, a specific example of an acquisition method of the second data 9 input to the neural network 7 will be described, in the case of magnetic resonance imaging. FIG. 6 illustrates an example of using provisional phase data calculated from the shift in resonance frequency (Larmor frequency) acquired using a shimming scan and the time of the echo center, as the second data. FIG. 7 illustrates an example of using indirect phase data that is the shift in resonance frequency acquired using a shimming scan, as the second data.

FIG. 6 illustrates the procedure of calculating the second data, using the shift in Larmor frequency acquired using an F0 map (shimming map) and the like, and the time up to when an echo is produced (TE time). As a basic principle, the phase of the nuclear spin is shifted as much as shift in Larmor frequency×time up to when an echo is produced (TE time). Hence, the estimated value of the phase is calculated by acquiring the shift in Larmor frequency and the TE time.

First, a sequence control circuit 220 of a magnetic resonance imaging device 200, which will be described below in FIG. 8, executes an F0 map (shimming map) estimation scan (step S100). Subsequently, with the second data generation function 110*h*, the processing circuit 110 that has acquired the collected data obtained by the F0 map estimation scan performed by the sequence control circuit 220, then generates a resonance frequency (Larmor frequency) shift map on the basis of the executed F0 map estimation scan (step S110). For example, the resonance frequency map is expressed in units of Hz.

Subsequently, the sequence control circuit 220 of the magnetic resonance imaging device 200 executes a collection pulse sequence for collecting medical images (step S120). Subsequently, with the second data generation function 110*h*, the processing circuit 110 obtains the relative time of the echo center of the pulse sequence executed at step S120, with respect to the zero phase (step S130). That is, the processing circuit 110 acquires the TE of the pulse sequence executed at step S120. Subsequently, with the second data generation function 110*h*, the processing circuit 110 calculates the product of the shift in resonance frequency obtained at step S110 and the time of the echo center obtained at step S130 as provisional phase data, and obtains the calculated data as the second data 9 (step S140).

That is, with the second data generation function 110*h*, the processing circuit 110 calculates the data obtained by multiplying the shift in resonance frequency at each location by the relative time of the echo center of the collection pulse sequence performed by the magnetic resonance imaging device 200, with respect to the zero phase, as the second data 9 that is the second input data for learning. For example, the shift in resonance frequency may also be obtained on the basis of a scan for estimating the shimming map, performed by the magnetic resonance imaging device 200.

With the first data generation function 110_g_, the processing circuit 110 may also generate the first data that is a medical image, on the basis of the collection pulse sequence collected at step S120.

The acquisition method of the second data 9 that is the second input data for learning is not limited to what has been described above. For example, with the second generation function 110_h_, the processing circuit 110 may also calculate the data representing the shift in resonance frequency at each location as indirect phase data, and obtain the calculated data as the second data 9 that is the second input data for learning.

A specific example of such a procedure is illustrated in FIG. 7. Because step S100 and step S110 in FIG. 7 are the same as those in FIG. 6, repeated description is omitted. At step S160, the processing circuit 110 calculates the shift in resonance frequency calculated at step S110 as indirect phase data, and obtains the calculated result as the second data 9 that is the second input data for learning.

As described above, the second data 9 plays an auxiliary role for image reconstruction, and an accurate phase value is not necessarily required for the second data 9. Thus, even the indirect phase data from which the processes at step S120 and step S130 in FIG. 6 are omitted, may also be used as the second data 9. That is, the second data 9 that is the second input data for learning may also be data representing the shift in resonance frequency at each location.

Moreover, the embodiment is not limited to the example described above. The second data 9 that is the second input data for learning may also be data representing the shift in resonance frequency at each location, and data obtained by multiplying the shift in resonance frequency at each location by the relative time of the echo center of the collection pulse sequence performed by the magnetic resonance imaging device 200, with respect to the zero phase. That is, both data described above may be input to the neural network 7 as the second data that is the pseudo-phase data.

As one example of using the data processing device 100, with reference to FIG. 8 and FIG. 9, a medical signal processing device incorporated with the data processing device 100 according to the embodiment will be described. The following description does not limit the use of the data processing device 100 to the medical signal processing device.

Figure 8:
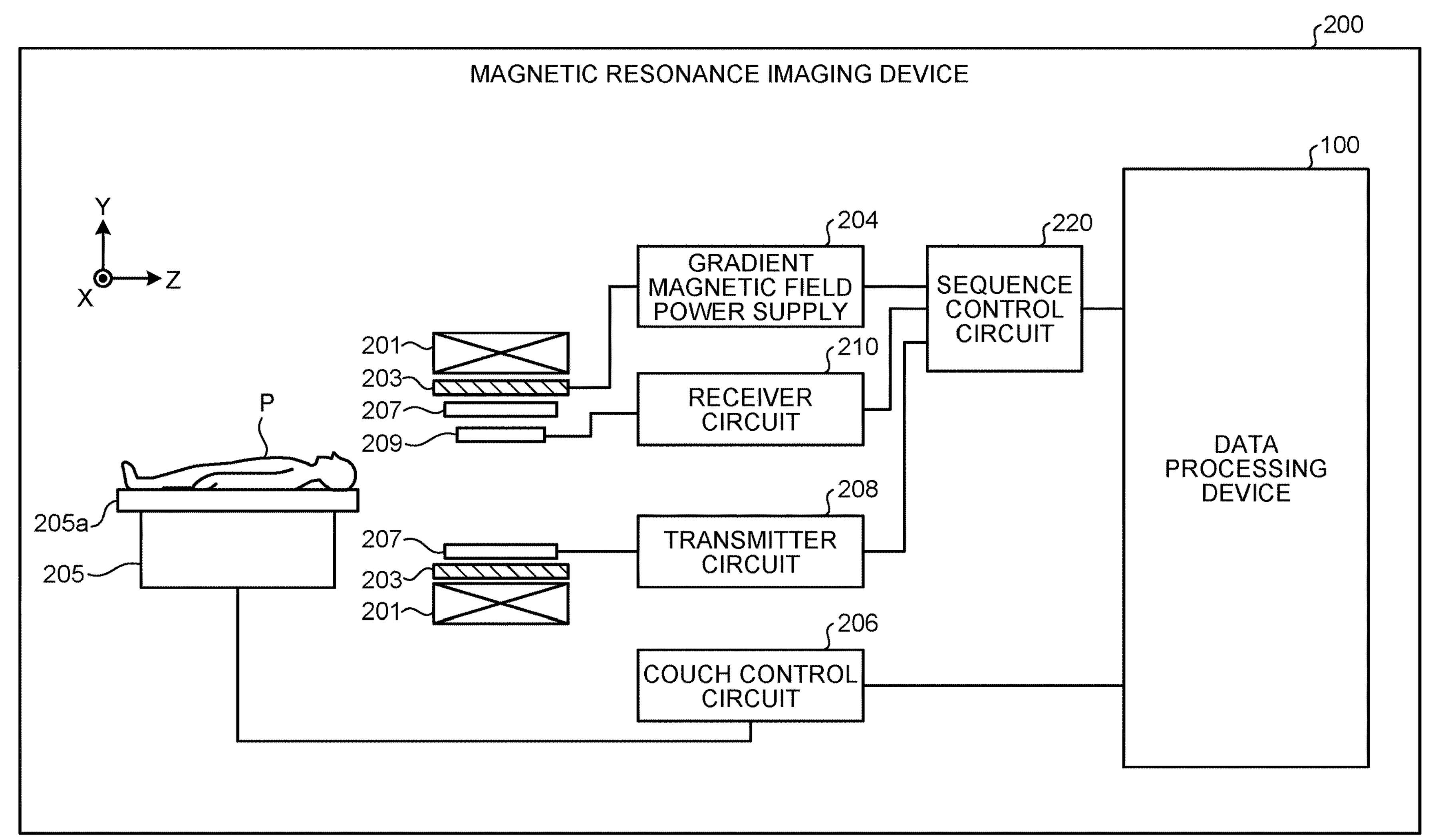
FIG. 8 is a diagram illustrating an example of a magnetic resonance imaging device according to the embodiment.
Figure 9:
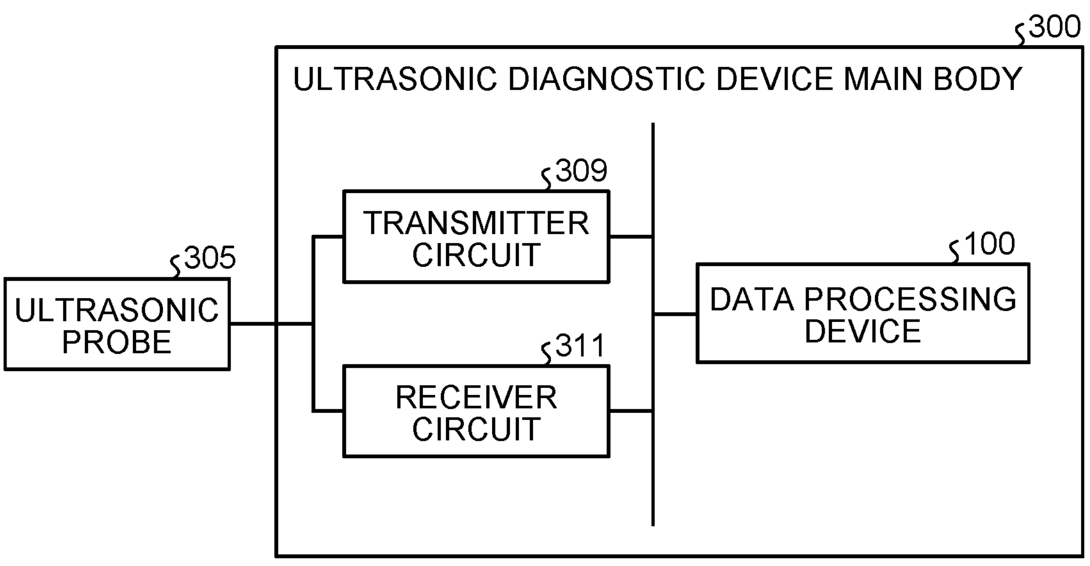
FIG. 9 is a diagram illustrating an example of an ultrasonic diagnostic device according to the embodiment.

That is, for example, the data processing device 100 is connected to various medical image diagnostic devices such as the magnetic resonance imaging device illustrated in FIG. 8 and the ultrasonic diagnostic device illustrated in FIG. 9. The data processing device 100 performs processing such as processing a signal received from the medical image diagnostic device, generating a learned model, and executing the learned model. Examples of the medical image diagnostic device to which the data processing device 100 is connected are not limited to the magnetic resonance imaging device and the ultrasonic diagnostic device, but may also be other devices such as an X-ray CT device and a PET device. As an example, the data processing device 100 may be a device for processing magnetic resonance data that is not medical data.

When the processing circuit 110 is incorporated in various medical image diagnostic devices, or when the processing is performed in conjunction with various medical image diagnostic devices, the processing circuit 110 may also have a function that can execute the process associated with the above.

FIG. 8 is an example of the magnetic resonance imaging device 200 incorporated with the data processing device 100 according to the embodiment.

As illustrated in FIG. 8, the magnetic resonance imaging device 200 includes a static magnetic field magnet 201, a static magnetic field power supply (not illustrated), a gradient coil 203, a gradient magnetic field power supply 204, a couch 205, a couch control circuit 206, a transmitter coil 207, a transmitter circuit 208, a receiver coil 209, a receiver circuit 210, the sequence control circuit 220 (sequence control unit), and the data processing device 100 described in FIG. 1. The magnetic resonance imaging device 200 does not include a subject P (for example, human body). Moreover, the configuration illustrated in FIG. 8 is merely an example.

The static magnetic field magnet 201 is a magnet formed in a substantially hollow cylindrical shape, and generates a static magnetic field in the interior space. For example, the static magnetic field magnet 201 is a superconducting magnet and the like, and is excited by receiving supply of electric current from the static magnetic field power supply. The static magnetic field power supply supplies electric current to the static magnetic field magnet 201. As another example, the static magnetic field magnet 201 may also be a permanent magnet. In this case, the magnetic resonance imaging device 200 need not be equipped with a static magnetic field power supply. Moreover, the static magnetic field power supply may be provided separately from the magnetic resonance imaging device 200.

The gradient coil 203 is a coil formed in a substantially hollow cylindrical shape, and is placed inside the static magnetic field magnet 201. The gradient coil 203 is formed by combining three coils corresponding to X, Y, and Z axes that are orthogonal to each other. These three coils individually receive electric current from the gradient magnetic field power supply 204, and generate gradient magnet fields in which the magnetic field intensity changes along the X, Y, and Z axes. For example, the gradient magnetic fields of the X, Y, and Z axes generated by the gradient coil 203 are a slice gradient magnetic field Gs, a phase encoding gradient magnetic field Ge, and a readout gradient magnetic field Gr. The gradient magnetic field power supply 204 supplies electric current to the gradient coil 203.

The couch 205 includes a couchtop 205_a_ on which the subject P is placed. Under the control of the couch control circuit 206, while the subject P is placed thereon, the couchtop 205_a_ is inserted into the cavity (imaging port) of the gradient coil 203. In general, the couch 205 is installed so that the longitudinal direction is parallel to the center axis of the static magnetic field magnet 201. Under the control of the data processing device 100, the couch control circuit 206 moves the couchtop 205_a_ in the longitudinal direction and the vertical direction, by driving the couch 205.

The transmitter coil 207 is placed inside the gradient coil 203, and a radio-frequency magnetic field is generated by receiving the supply of RF pulses from the transmitter circuit 208. The transmitter circuit 208 supplies RF pulses corresponding to the Larmor frequency that is determined by the type of target atom and the magnetic field intensity, to the transmitter coil 207.

The receiver coil 209 is placed inside the gradient coil 203 to receive a magnetic resonance signal (hereinafter, referred to as an "MR signal" as necessary) emitted from the subject P under the influence of a radio-frequency magnetic field. Upon receiving the magnetic resonance signal, the receiver coil 209 outputs the received magnetic resonance signal to the receiver circuit 210.

The transmitter coil 207 and the receiver coil 209 described above are merely examples. The transmitter coil 207 and the receiver coil 209 may be configured by combining one or a plurality of a coil equipped only with a transmission function, a coil equipped only with a reception function, and a coil equipped with transmission and reception functions.

The receiver circuit 210 detects the magnetic resonance signal output from the receiver coil 209, and generates magnetic resonance data on the basis of the detected magnetic resonance signal. More specifically, the receiver circuit 210 generates magnetic resonance data by digitally converting the magnetic resonance signal output from the receiver coil 209. Moreover, the receiver circuit 210 transmits the generated magnetic resonance data to the sequence control circuit 220. The receiver circuit 210 may also be provided on the side of the gantry device including the static magnetic field magnet 201, the gradient coil 203, and the like.

On the basis of sequence information, the sequence control circuit 220 drives the gradient magnetic field power supply 204, the transmitter circuit 208, and the receiver circuit 210 to capture images of the subject P. In this example, the sequence information is information that defines the procedure for imaging. In the sequence information, the intensity of electric current supplied to the gradient coil 203 by the gradient magnetic field power supply 204 and the timing at which the electric current is supplied, the intensity of the RF pulse supplied to the transmitter coil 207 by the transmitter circuit 208 and the timing at which the RF pulse is applied, and the timing at which the magnetic resonance signal is detected by the receiver circuit 210, and the like are defined. For example, the sequence control circuit 220 is an integrated circuit such as an application specific integrated circuit (ASIC) and a field programmable gate array (FPGA), and an electronic circuit such as a central processing unit (CPU) and a micro processing unit (MPU). The sequence control circuit 220 is an example of a scanning unit.

Moreover, upon receiving magnetic resonance data from the receiver circuit 210 as a result of capturing an image of the subject P by driving the gradient magnetic field power supply 204, the transmitter circuit 208, and the receiver circuit 210, the sequence control circuit 220 transfers the received magnetic resonance data to the data processing device 100. In addition to the processing described in FIG. 1, the data processing device 100 performs the overall control of the magnetic resonance imaging device 200.

Returning to FIG. 1, the processing performed by the data processing device 100 and that is different from the processing described in FIG. 1 will be described. With the interface function 110*c*, the processing circuit 110 transmits sequence information to the sequence control circuit 220, and receives magnetic resonance data from the sequence control circuit 220. Moreover, upon receiving the magnetic resonance data, the processing circuit 110 with the interface function 110*c* stores the received magnetic resonance data in the memory 132.

With the control function 110*d*, the magnetic resonance data stored in the memory 132 is disposed in k-space. As a result, the memory 132 stores the k-space data.

The memory 132 stores the magnetic resonance data received by the processing circuit 110 with the interface function 110*c*, the k-space data disposed in the k-space by the processing circuit 110 with the control function 110*d*, image data generated by the processing circuit 110 with the generation function (or the application function 110*e*), and the like.

With the control function 110*d*, the processing circuit 110 performs the overall control of the magnetic resonance imaging device 200, and controls imaging, the generation of an image, the display of the image, and the like. For example, the processing circuit 110 with the control function 110*d* receives an input of imaging conditions (imaging parameters and the like) on the GUI, and generates sequence information according to the received imaging conditions. Moreover, the processing circuit 110 with the control function 110*d* transmits the generated sequence information to the sequence control circuit 220.

With the generation function not illustrated in FIG. 1 (or the application function 110*e*), the processing circuit 110 generates a magnetic resonance image, by reading the k-space data from the memory 132 and applying reconstruction processing such as Fourier transform on the read k-space data.

FIG. 9 is a configuration example of an ultrasonic diagnostic device main body 300 incorporated with the data processing device 100 according to the embodiment. The ultrasonic diagnostic device according to the embodiment includes an ultrasonic probe 305 and the ultrasonic diagnostic device main body 300. The ultrasonic diagnostic device main body 300 includes a transmitter circuit 309, a receiver circuit 311, and the data processing device 100 described above.

The ultrasonic probe 305 has a plurality of piezoelectric transducer elements. The piezoelectric transducer elements generate ultrasonic waves on the basis of a drive signal supplied from the transmitter circuit 309 included in the ultrasonic diagnostic device main body 300, which will be described below. The piezoelectric transducer elements in the ultrasonic probe 305 receive reflected waves from the subject P, and convert the received reflected waves into electrical signals (reflected wave signals). The ultrasonic probe 305 has a matching layer on the piezoelectric transducer element, a backing material that prevents the ultrasonic waves from propagating from the piezoelectric transducer element to the rear, and the like. The ultrasonic probe 305 is detachably connected to the ultrasonic diagnostic device main body 300. Moreover, the ultrasonic probe 305 is an example of a scanning unit.

When ultrasonic waves are transmitted from the ultrasonic probe 305 to the subject P, the transmitted ultrasonic waves are reflected successively by the discontinuous surface of the acoustic impedance in the body tissue of the subject P, received by the piezoelectric transducer elements of the ultrasonic probe 305, and are converted into reflected wave signals. The amplitude of the reflected wave signal depends on the difference in acoustic impedance on the discontinuous surface that reflects the ultrasonic waves. When the transmitted ultrasonic pulse is reflected by the moving blood flow or the surface of the heart wall or the like, the reflected wave signal depends on the velocity component of the moving body with respect to the ultrasonic wave transmission direction due to Doppler effect, and undergoes a frequency shift.

The ultrasonic diagnostic device main body 300 is a device that generates ultrasonic image data on the basis of the reflected wave signal received from the ultrasonic probe

305. The ultrasonic diagnostic device main body 300 is a device capable of generating two-dimensional ultrasonic image data on the basis of a two-dimensional reflected wave signal, and that is capable of generating three-dimensional ultrasonic image data on the basis of a three-dimensional reflected wave signal. However, the embodiment is applicable even if the ultrasonic diagnostic device main body 300 is a device dedicated to two-dimensional data.

As illustrated in FIG. 9, the ultrasonic diagnostic device main body 300 includes the transmitter circuit 309, the receiver circuit 311, and the data processing device 100.

The transmitter circuit 309 and the receiver circuit 311 control the ultrasonic transmission and reception performed by the ultrasonic probe 305, on the basis of the instruction of the data processing device 100 with a control function. The transmitter circuit 309 includes a pulse generator, a transmission delay unit, a pulser, and the like, and supplies a drive signal to the ultrasonic probe 305. The pulse generator repeatedly generates a rate pulse for forming transmission ultrasonic waves at a certain pulse repetition frequency (PRF). Moreover, the transmission delay unit provides a delay time of each piezoelectric transducer element necessary for focusing the ultrasonic waves generated from the ultrasonic probe 305 into a beam shape and for determining the transmission directivity, to each rate pulse generated by the pulse generator. Furthermore, the pulser applies a drive signal (drive pulse) to the ultrasonic probe 305 at a timing based on the rate pulse.

That is, the transmission delay unit optionally adjusts the transmission direction of the ultrasonic waves transmitted from the piezoelectric transducer element surface, by changing the delay time provided to each rate pulse. Moreover, the transmission delay unit controls the position of the focusing point (transmission focus) in the depth direction of the ultrasonic wave transmission, by changing the delay time provided to each rate pulse.

Furthermore, the receiver circuit 311 includes an amplifier circuit, an analog/digital (A/D) converter, a reception delay circuit, an adder, a quadrature detection circuit, and the like, and generates a receiver signal (reflected wave data), by performing various processes on the reflected wave signal received from the ultrasonic probe 305. The amplifier circuit performs gain correction processing by amplifying the reflected wave signal for each channel. The A/D converter performs A/D conversion on the gain-corrected reflected wave signal. The reception delay circuit provides a reception delay time necessary for determining the reception directivity to digital data. The adder performs addition processing on the reflected wave signal to which the reception delay time is given by the reception delay circuit. The addition processing of the adder emphasizes the reflected component from the direction corresponding to the reception directivity of the reflected wave signal. Then, the quadrature detection circuit converts the output signal of the adder into an in-phase signal (I signal, I: In-phase) and a quadrature signal (Q signal, Q: Quadrature-phase) in the baseband. Then, the quadrature detection circuit transmits the I signal and Q signal (hereinafter referred to as IQ signals) to the processing circuit 110 as reception signals (reflected wave data). The quadrature detection circuit may also convert the output signal of the adder into a radio frequency (RF) signal and transmit the RF signal to the processing circuit 110. The IQ signal and the RF signal will be reception signals with phase information.

To scan a two-dimensional region in the subject P, the transmitter circuit 309 causes the ultrasonic probe 305 to transmit an ultrasonic beam for scanning the two-dimensional region. Then, the receiver circuit 311 generates a two-dimensional reception signal from the two-dimensional reflected wave signal received from the ultrasonic probe 305. Moreover, to scan a three-dimensional region in the subject P, the transmitter circuit 309 causes the ultrasonic probe 305 to transmit an ultrasonic beam for scanning the three-dimensional region. Then, the receiver circuit 311 generates a three-dimensional reception signal from the three-dimensional reflected wave signal received from the ultrasonic probe 305. The receiver circuit 311 generates a receive signal on the basis of the reflected wave signal, and transmits the generated reception signal to the processing circuit 110.

The transmitter circuit 309 causes the ultrasonic probe 305 to transmit an ultrasonic beam from a predetermined transmission position (transmission scanning line). At a predetermined reception position (reception scanning line), the receiver circuit 311 receives a signal based on the reflected wave of the ultrasonic wave beam transmitted from the transmitter circuit 309, from the ultrasonic probe 305. In the case of not performing parallel simultaneous reception, the transmission scanning line and the reception scanning line become the same scanning line. On the other hand, in the case of performing parallel simultaneous reception, when the transmitter circuit 309 causes the ultrasonic probe 305 to transmit one ultrasonic beam through one transmission scanning line, the receiver circuit 311 simultaneously receives the signal based on the reflected wave derived from the ultrasonic wave transmitted to the ultrasonic probe 305 by the transmitter circuit 309 at a plurality of predetermined reception positions (reception scanning lines) as a plurality of reception beams via the ultrasonic probe 305.

According to at least one of the embodiments described above, it is possible to improve the image quality.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data processing device, comprising:

processing circuitry configured to generate output data by inputting, to a learned model, as input data, both first input data of a complex value and second input data that is data related to a complex phase, the learned model having been trained using, as training input data, first input data for learning of a complex value obtained based on collected data collected by a medical image diagnostic device and second input data for learning that is data related to a complex phase of the collected data, and using, as training output data, output data for learning, wherein the medical image diagnostic device is a magnetic resonance imaging device or an ultrasonic diagnostic apparatus.

2. The data processing device according to claim 1, wherein the medical image diagnostic device is a magnetic resonance imaging device, and the second input data for learning is data obtained by multiplying a shift in resonance frequency at each location by a relative time of an echo center of a collection pulse sequence performed by the magnetic resonance imaging device, with respect to a zero phase.

3. The data processing device according to claim 1, wherein the medical image diagnostic device is a magnetic resonance imaging device, and the second input data for learning is data representing a shift in resonance frequency at each location.

4. The data processing device according to claim 1, wherein the medical image diagnostic device is a magnetic resonance imaging device, and the second input data for learning is data representing a shift in resonance frequency at each location, and data obtained by multiplying the shift in the resonance frequency at each location by a relative time of an echo center of a collection pulse sequence performed by the magnetic resonance imaging device, with respect to a zero phase.

5. The data processing device according to claim 2, wherein the shift in the resonance frequency is obtained based on scanning for estimating a shimming map performed by the magnetic resonance imaging device.

6. The data processing device according to claim 1, wherein the output data for learning is data from which noise is reduced compared to the first input data for learning.

7. The data processing device according to claim 1, wherein the output data for learning is data representing segment information at each location of the first input data for learning.

8. The data processing device according to claim 1, wherein the learned model is a learned model that outputs the output data by taking data consistency into consideration.

9. The data processing device according to claim 1, wherein the learned model is a learned model to which an automated transform by manifold approximation (AUTOMAP) method is applied.

10. A magnetic resonance imaging device that collects data, the magnetic resonance imaging device comprising:

sequence control circuitry configured to execute a pulse sequence, and a processing circuit configured to generate output data by inputting both first input data of a complex value and second input data that is data related to a complex phase obtained by the pulse sequence as input data, to a learned model that has been trained using first input data for learning of a complex value obtained based on the collected data and second input data for learning that is data related to a complex phase of the collected data as training input data, and using output data for learning as training output data.

11. A data processing method, comprising:

generating output data by inputting, to a learned model, as input data, both first input data of a complex value and second input data that is data related to a complex phase, the learned model having been trained using, as training input data, first input data for learning of a complex value obtained based on collected data collected by a medical image diagnostic device and second input data for learning that is data related to a complex phase of the collected data, and using, as training output data, output data for learning, wherein the medical image diagnostic device is a magnetic resonance imaging device or an ultrasonic diagnostic apparatus.

* * * * *